US010709392B2

(12) United States Patent
Ou et al.

(10) Patent No.: US 10,709,392 B2
(45) Date of Patent: *Jul. 14, 2020

(54) SENSOR FAULT DETECTION USING ANALYTE SENSOR DATA PATTERN COMPARISON

(71) Applicant: ABBOTT DIABETES CARE INC., Alameda, CA (US)

(72) Inventors: Junli Ou, Pleasanton, CA (US); Erwin Satrya Budiman, Fremont, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/110,663

(22) Filed: Aug. 23, 2018

(65) Prior Publication Data

US 2018/0360391 A1    Dec. 20, 2018

Related U.S. Application Data

(63) Continuation of application No. 14/771,804, filed as application No. PCT/US2014/026845 on Mar. 13, 2014, now Pat. No. 10,076,285.

(60) Provisional application No. 61/794,793, filed on Mar. 15, 2013.

(51) Int. Cl.
*A61B 5/00* (2006.01)
*A61B 5/145* (2006.01)
*A61B 5/1459* (2006.01)

(52) U.S. Cl.
CPC ........ *A61B 5/7271* (2013.01); *A61B 5/14532* (2013.01); *A61B 5/742* (2013.01); *A61B 5/1459* (2013.01); *A61B 2560/0228* (2013.01)

(58) Field of Classification Search
CPC ....... A61B 5/00; A61B 5/145; A61B 5/14532; A61B 5/7271; A61B 5/742; A61B 5/1459; A61B 2560/0228
See application file for complete search history.

(56) References Cited

U.S. PATENT DOCUMENTS

| 4,772,445 A | * | 9/1988 | Nasrallah | G01D 3/02 |
| | | | | 318/563 |
| 9,317,657 B2 | * | 4/2016 | Breton | A61B 5/0002 |
| 2014/0182350 A1 | * | 7/2014 | Bhavaraju | G01M 99/008 |
| | | | | 73/1.02 |

\* cited by examiner

*Primary Examiner* — Eric J Messersmith
(74) *Attorney, Agent, or Firm* — Vorys, Sater, Seymour and Pease LLP

(57) ABSTRACT

Analyte sensor faults are detected. Datasets of glucose values sensor electronics are coupled to a glucose sensor in fluid contact with interstitial fluid under a skin surface. Baseline median glucose value and glucose variability values are computed, based on the first dataset. A baseline data point is stored. Evaluation median glucose value and variability are computed, based on the second dataset of glucose values. An evaluation data point is stored. A magnitude of a vector that extends between the baseline data point and the evaluation data point is computed. A component of the magnitude of the vector that is parallel to a hypoglycemia risk contour line is computed and compared to a predefined threshold value. An indication that a sensor fault has been detected if the component is greater than a threshold is displayed.

19 Claims, 11 Drawing Sheets

SENSOR FAULT DETECTION USING ANALYTE SENSOR DATA PATTERN COMPARISON

CROSS REFERENCE TO RELATED APPLICATIONS

This application is a continuation of U.S. patent application Ser. No. 14/771,804 filed on Sep. 1, 2015, which is a U.S. National Stage Entry of International Application No. PCT/US2014/026845 filed on Mar. 13, 2014, which claims the benefit of U.S. Provisional Patent Application No. 61/794,793 filed on Mar. 15, 2013, which are expressly incorporated by reference herein in their entirety.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte time series characteristics, such as glucose levels, in bodily fluids such as in the blood stream or in interstitial fluid. Some of these analyte level measuring devices are configured so that at least a portion of a sensor of an on-body device is positioned below a skin surface of a user, e.g., in a blood vessel or in the subcutaneous tissue of a user. As used herein, the term analyte monitoring system is used to refer to any type of in vivo monitoring system that uses a sensor disposed with at least a subcutaneous portion to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a prompt or request signal from a processor/display unit (e.g., based on an activation action and/or proximity using, for example, a near field communications protocol).

In some cases, analyte monitoring systems have been found to occasionally provide false readings due to one or more error conditions. In such instances, the analyte monitoring systems maybe described as operating in a fault mode. End of sensor life and early signal attenuation (ESA) are two examples of fault modes where false readings may occur. A decaying sensor signal due to sensor removal, patch adhesive issues, and depleted sensing chemistry are examples of causes of false readings at the end of a sensor's life. Prior art methods of detecting fault modes typically rely on in vivo calibration that compares the sensor's output with one or more in vitro reference glucose readings. Using several in vitro reference glucose readings, both the calibration factor and fault modes such as end of sensor life and ESA can be determined/detected. However, using in vitro reference glucose readings typically requires user interaction, uncomfortable "finger stick" blood samples, a supply of relatively costly test strips, and a meter that can read the test strips. Thus, what is needed are systems, methods and apparatus that do not rely on in vitro reference glucose readings to detect fault modes such as end of sensor life and ESA.

SUMMARY

The present disclosure provides systems, methods, and apparatus that allow a user (e.g., a health care provider, patient, etc.) to analyze a collection of analyte monitoring system sensor data to identify or detect sensor faults. Some embodiments of the present disclosure include computer-implemented methods of identifying sensor fault modes using analyte monitoring system sensor data. The methods include receiving first and second datasets of glucose values from sensor electronics operatively coupled to transcutaneously positioned glucose sensors, computing a baseline median glucose value and a baseline glucose variability value based on the first dataset, storing a baseline data point, computing an evaluation median glucose value and an evaluation glucose variability value based on the second dataset of glucose values, storing an evaluation data point, computing a magnitude of a vector that extends between the baseline data point and the evaluation data point, computing a component of the magnitude of the vector that is parallel to a hypoglycemia risk contour line, comparing the component to a predefined threshold value, and displaying an indication that a sensor fault has been detected if the component is greater than a threshold.

Embodiments of the present disclosure also include a computer system and a computer program product for identifying sensor fault modes using analyte monitoring system sensor data. Numerous other aspects and embodiments are provided. Other features and aspects of the present disclosure will become more fully apparent from the following detailed description, the appended claims, and the accompanying drawings.

BRIEF DESCRIPTION OF THE DRAWINGS

The accompanying drawings, which are incorporated herein, form part of the specification. Together with this written description, the drawings further serve to explain the principles of, and to enable a person skilled in the relevant arts, to make and use the present disclosure.

DETAILED DESCRIPTION

Figure 1:
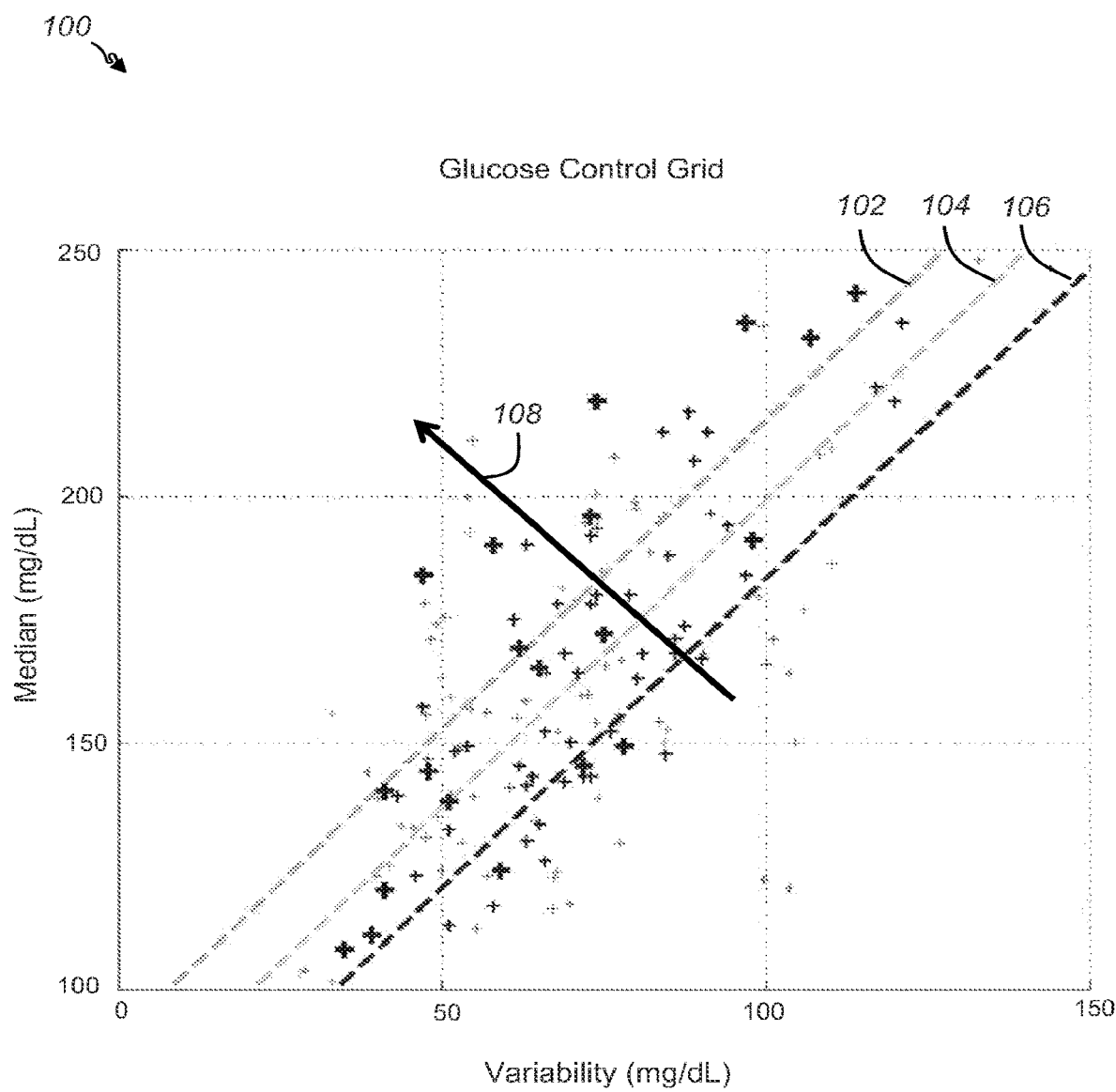
FIG. 1 depicts an example control grid in accordance with some embodiments of the present disclosure.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

The present disclosure provides systems, methods, and apparatus to identify sensor fault modes using sensor data from an analyte monitoring system, such as, for example, any type of in vivo monitoring system that uses a sensor disposed with at least a subcutaneous portion to measure and store sensor data representative of analyte concentration levels automatically over time. Analyte monitoring systems may include CGMs which are programmed to transmit sensor data according to a predetermined transmission schedule, continuously, or at regular time intervals to a processor/display unit and systems that transfer stored sensor data in one or more batches in response to a request from a processor/display unit, i.e., not according to a predetermined transmission schedule. Without requiring a patient to provide blood samples for in vitro reference glucose readings, the present disclosure is operable to identify sensor faults from data from an in vivo analyte sensor.

According to some embodiments of the present disclosure, a dataset representative of a patient's monitored analyte concentration level (herein referred to as "sensor data") over time is received from sensor electronics operatively coupled to an analyte sensor in fluid contact with interstitial fluid. The measurements, especially those of the patient's analyte concentration level, are characterized by a pair of metrics. This pair provides a representation of the static and dynamic level of analyte control over a window of time. There are paired values that are physiologically feasible, and there are those that are very unlikely to be physiologically feasible. In addition, when comparing paired values from one window of time against another, the change in the quantities may or may not be physiologically feasible. The approach described herein identifies value pairs on a given measurement window and/or changes in value pairs among several measurement windows to detect non physiological changes indicative of a sensor fault. A metric for static analyte state is the median value of the sensor data. A metric for dynamic analyte state is the difference between the median and the tenth percentile values of the same sensor data, referred to herein as a variability value.

When sensor data obtained over a window of time is first obtained, a baseline pair can be calculated. A baseline median or average analyte value and a baseline analyte variability value are computed from this dataset. These baseline values are used as coordinates to plot a baseline data point on an analyte control grid. Once a second, subsequent dataset is received from the sensor electronics that does not include a significant number of analyte values that are also in the first dataset, an evaluation data point is plotted on the control grid. The evaluation data point is determined by computing an evaluation median or average analyte value and an evaluation analyte variability value from the second dataset. Next, the magnitude of a vector that extends from the baseline data point to the evaluation data point is computed. Since any change in the value pair between the evaluation and baseline points may arise due to both true physiological change, such as the patient's ability to improve glycemic control, and a sensor fault, such as ESA, a mechanism is needed to isolate the latter for detection. For example, for sensing glucose, one method is to observe how patients can change their state of glycemic control over time, and correlate it with physiology-derived gradients that characterize this change. Examples of these gradients include gradients that quantify clinical risks such as hypoglycemia risk, retinopathy risk, or diabetic ketoacidosis risk. In some embodiments, contour lines representing varying degrees of hypoglycemic risk can be plotted on the control grid. Plotted contour lines can be used to graphically approximate the contour line that passes on to any point in the control grid. Alternatively, an analytical expression of these contour lines can be expressed in terms of a gradient function. In that case, the determination of a contour line passing through any point in the control grid is done by evaluating the gradient function. Next, a component of the magnitude of the vector between the points that is parallel to a hypoglycemia risk contour line is computed. In other words, a projection of the vector on the hypoglycemic risk contour line is computed. The component of the vector is compared to a predetermined threshold value. Values smaller than the threshold value indicate that the sensor is operating within an acceptable range. Values larger than the threshold value indicate that the sensor is operating in a fault mode or has reached the end of its operating life. The user is alerted to the fault condition and can be directed to replace the sensor. Alternatively, one or more reference measurements may be requested and a larger threshold value may be used to evaluate the status of the sensor. If the component of the vector is smaller than the larger threshold value, then the system indicates no failure detected. If the component of the vector is larger than the larger threshold value, then the system indicates the sensor should be replaced.

The invention may be applied to any analyte concentration level determination system that may exhibit or at least be suspected of exhibiting, or that may be susceptible to, in vivo sensor faults. Embodiments of the invention are described primarily with respect to continuous glucose monitoring devices and systems but the present disclosure may be applied to other analytes and analyte characteristics, as well as data from measurement systems that transmit sensor data from a sensor unit to another unit such as a processing or display unit in response a request from the other unit. For example, other analytes that may be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times. The present disclosure also provides numerous additional embodiments.

Embodiments of the present disclosure may include a programmed computer system adapted to receive and store data from an analyte monitoring system. The computer system may include one or more processors for executing instructions or programs that implement the methods described herein. The computer system may include memory and persistent storage devices to store and manipulate the instructions and sensor data received from the analyte monitoring system. The computer system may also include communications facilities (e.g., wireless and/or wired) to enable transfer of the sensor data from the analyte monitoring system to the computer. The computer system may include a display and/or output devices for identifying dropouts in the sensor data to a user. The computer system may include input devices and various other components (e.g., power supply, operating system, clock, etc.) that are typically found in a conventional computer system. In some embodiments, the computer system may be integral to the analyte monitoring system. For example, the computer system may be embodied as a handheld or portable receiver unit within the analyte monitoring system.

The various methods described herein for performing one or more processes also described herein may be embodied as computer programs (e.g., computer executable instructions and data structures) developed using an object oriented programming language that allows the modeling of complex systems with modular objects to create abstractions that are representative of real world, physical objects and their interrelationships. However, any practicable programming language and/or techniques may be used. The software for performing the inventive processes, which may be stored in a memory or storage device of the computer system described herein, may be developed by a person of ordinary skill in the art based upon the present disclosure and may include one or more computer program products. The computer program products may be stored on a computer readable medium such as a server memory, a computer network, the Internet, and/or a computer storage device.

Turning now to FIG. 1, an example of a control grid 100 that depicts the states of patients with diabetes mellitus is shown. In the particular example shown, the control grid 100 provides a plot of a patients' glucose variability (on the x-axis) versus patients' median glucose concentration level (on the y-axis). Thus, each point is generated from a patient's sensor glucose data. In general, the patient's glycemic variability and median glucose are highly correlated. Contour or hypoglycemia risk lines 102, 104, 106 indicate a hypoglycemia risk gradient across the area of the control grid 100. In other words, moving in the direction of the solid arrow which is perpendicular to the hypoglycemia risk lines 102, 104, 106, each risk line 102, 104, 106 indicates a decreasing level of hypoglycemia risk for the patients whose plotted points lie closer to the upper left portion of the control grid. Thus, risk line 102 represents low hypoglycemia risk, risk line 104 represents intermediate hypoglycemia risk, and risk line 106 represents high hypoglycemia risk.

As a result of the correlation between glycemic variability and median glucose, patient data clusters in the band parallel to the hypoglycemia risk lines 102, 104, 106. The derivation and determination of the hypoglycemia risk lines 102, 104, 106 is described in detail in PCT Application No. PCT/US/2011/066610, filed on Dec. 21, 2011, entitled "Feedback for Cloud or HCP to Payer or Patient via Meter or Cellphone," and hereby incorporated herein by reference for all purposes.

Figure 2:
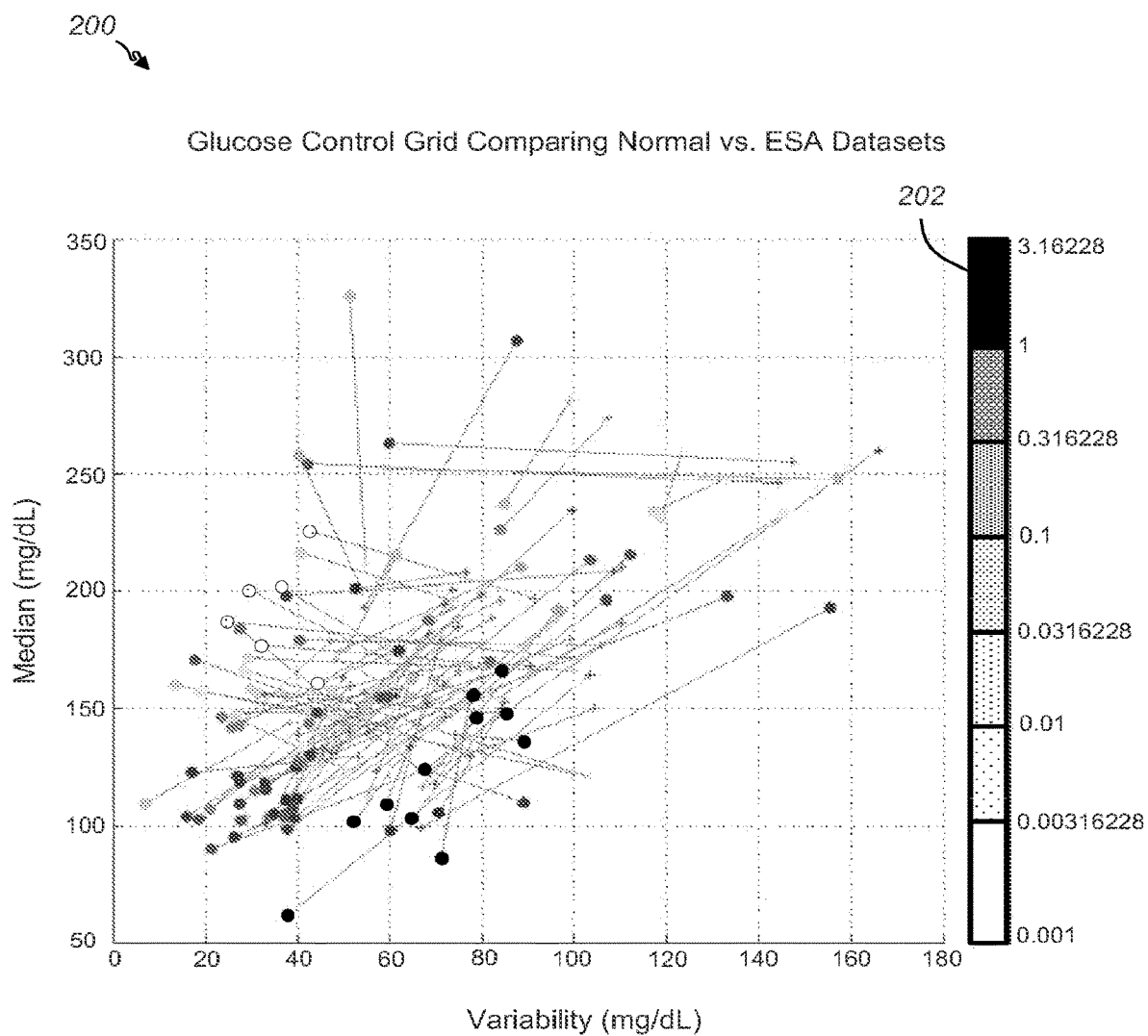
FIG. 2 depicts the example control grid of FIG. 1 with additional information in accordance with some embodiments of the present disclosure.
Figure 3:
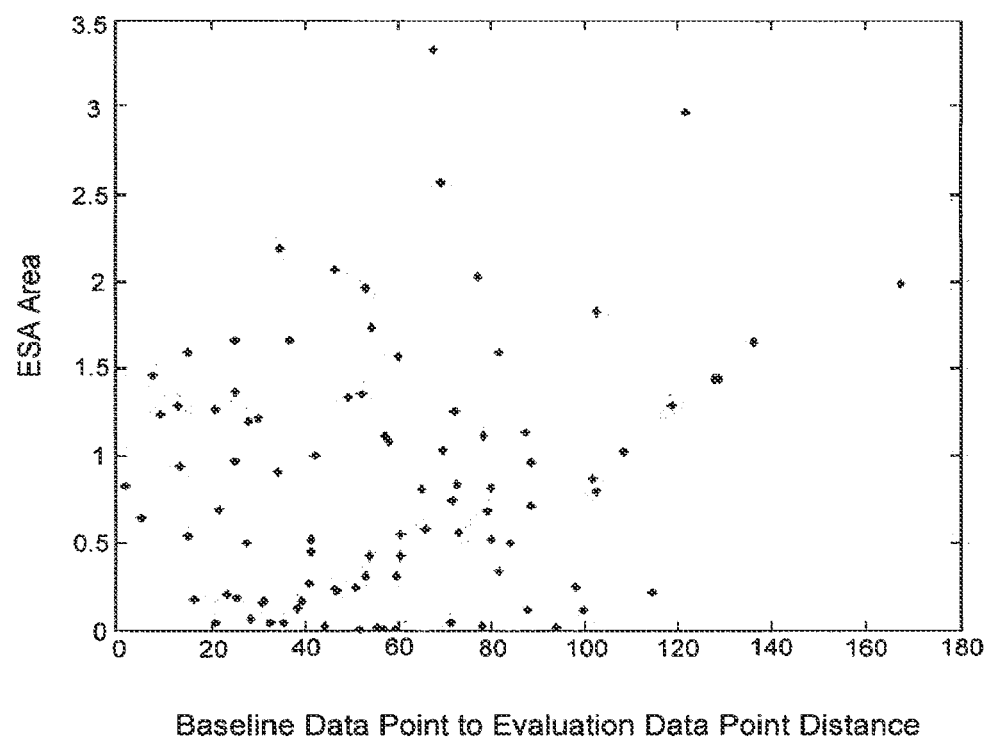
FIG. 3 depicts a graph of ESA severity versus baseline data point to evaluation data point distance in accordance with some embodiments of the present disclosure.
Figure 4A:
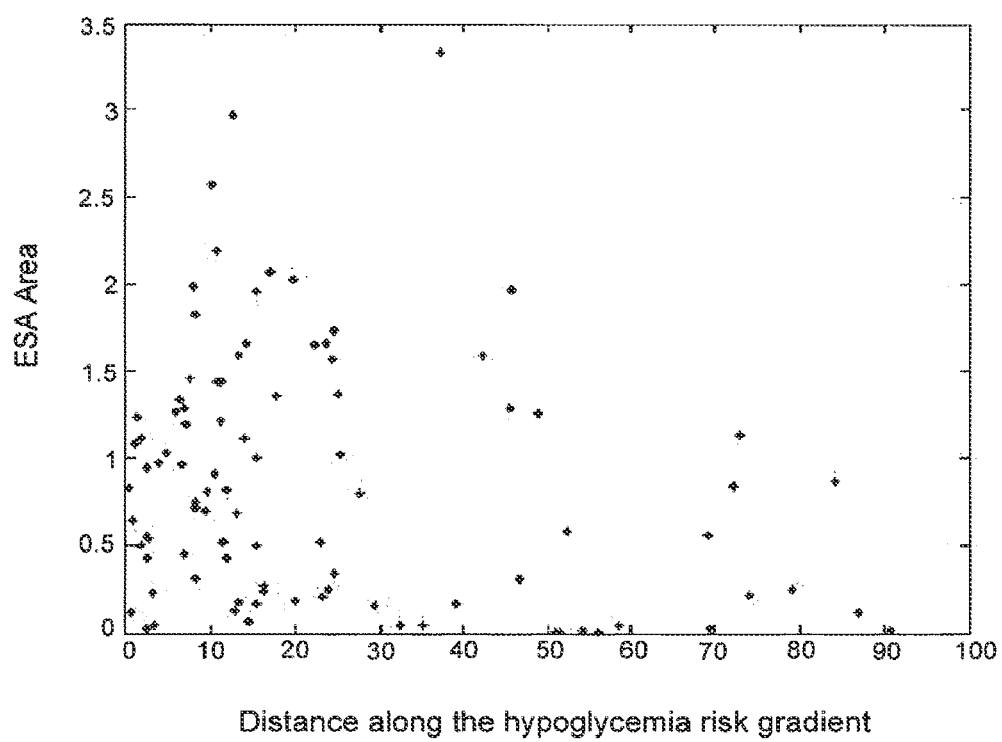
FIG. 4A depicts a graph of ESA severity versus distance along the hypoglycemia risk gradient in accordance with some embodiments of the present disclosure.

Turning to FIG. 2, a control grid 200 with the same patient data from FIG. 1 is shown but further including points (paired via a connecting line to the original points) that represent earlier sensor data from the same sensor that generated the data for the original points. The original points shift position on the control grid 200 towards the circle icons. The presence and severity of early signal attenuation (ESA) is represented by an ESA area metric and a scale 202. Darker denser patterns in the circle icons represent more severe ESA than circle icons with lighter less dense patterns. The distance between control grid values represented by the connecting lines in FIG. 2 for each sensor dataset can be compared against the ESA Area metric of the corresponding points. In general, sensors whose early wear period experiences more ESA, as represented by a larger ESA area, have larger late-to-early control grid distances. This correlation is illustrated in the graph 300 of FIG. 3. Examination of the data reveals that the component of this late-to-early distance perpendicular to the hypoglycemia risk lines (i.e. along the direction of the hypoglycemia risk gradient) has poor correlation to the ESA Area metric as shown in the graph 400A of FIG. 4A.

Figure 4B:
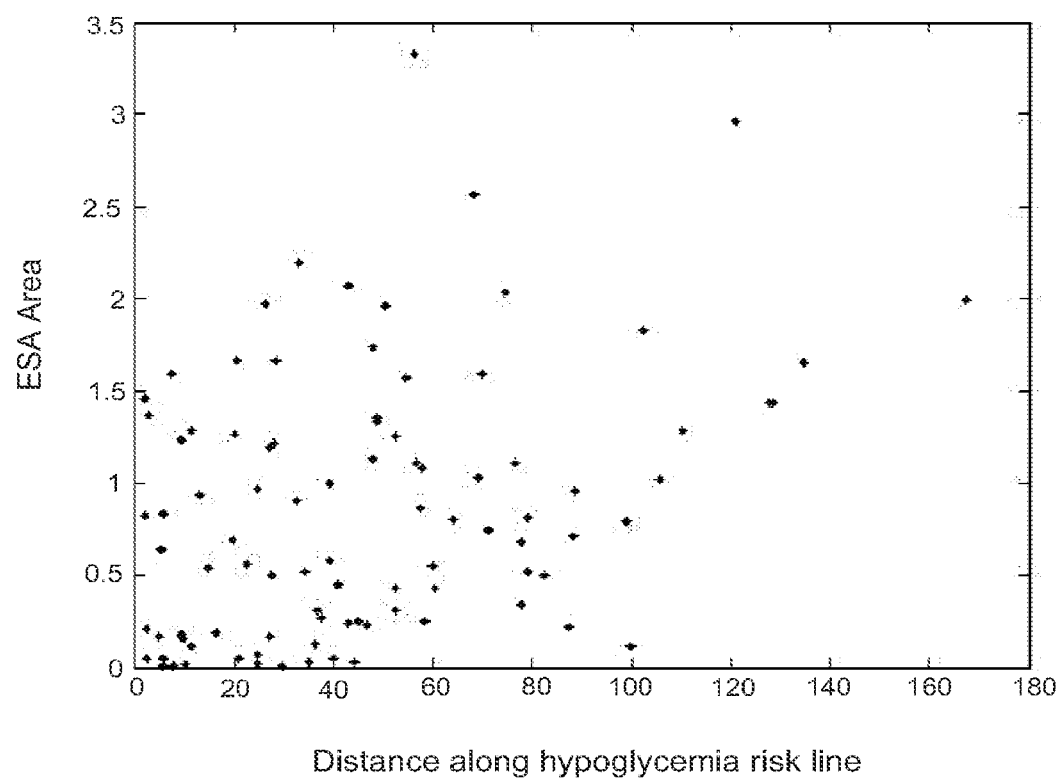
FIG. 4B depicts a graph of ESA severity versus distance along a hypoglycemia risk line in accordance with some embodiments of the present disclosure.

However, using only the component of the late-to-early distance along the hypoglycemia risk lines, the correlation to the ESA Area metric is improved. This can be seen by comparing the potential false positives when detecting ESA using a high value threshold based on the x-axis values of FIG. 4B as opposed to using a high value threshold based on the x-axis values of FIG. 4A. In other words, a vertical line can be drawn on the graph 400B of FIG. 4B that represents a threshold above which only points corresponding to severe ESA faults exist whereas no such line can be drawn on the graph 400A of FIG. 4A.

The present disclosure uses the above-described observations to recognize when a sensor is providing data that indicates the sensor is operating in a fault mode such as ESA or end of sensor life. When the projection of a vector from a baseline data point plotted on a control grid (e.g., depicting median analyte value versus analyte variability) to an evaluation point plotted on the same grid, along a risk line (e.g., a contour line of a risk gradient such as for example a hypoglycemia risk gradient), is larger than a threshold amount, the system of the present disclosure is operative to determine that the sensor is operating in a fault mode.

Figure 5A:
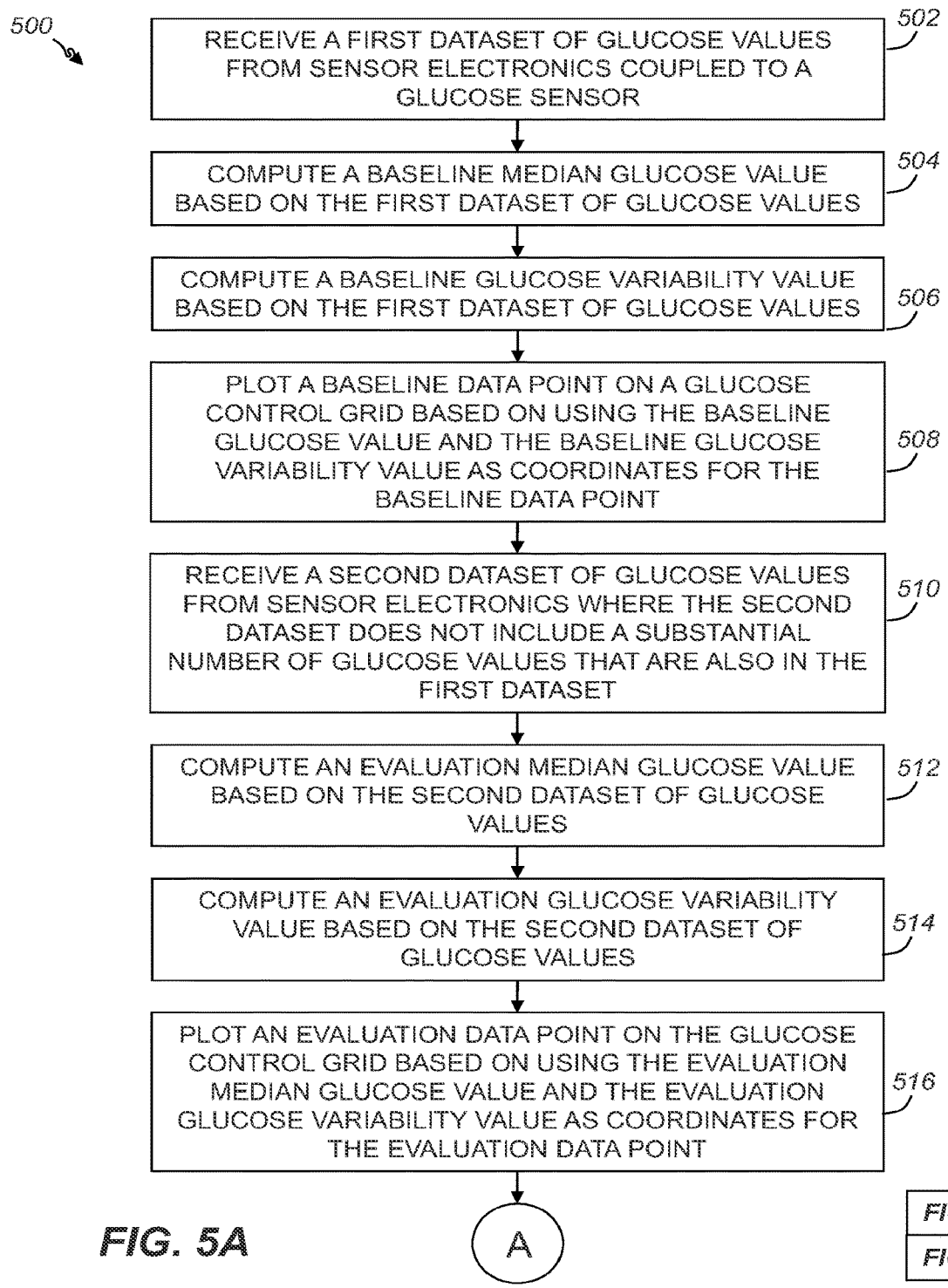
FIGS. 5A and 5B depict a flowchart illustrating an example method in accordance with some embodiments of the present disclosure.
Figure 5B:
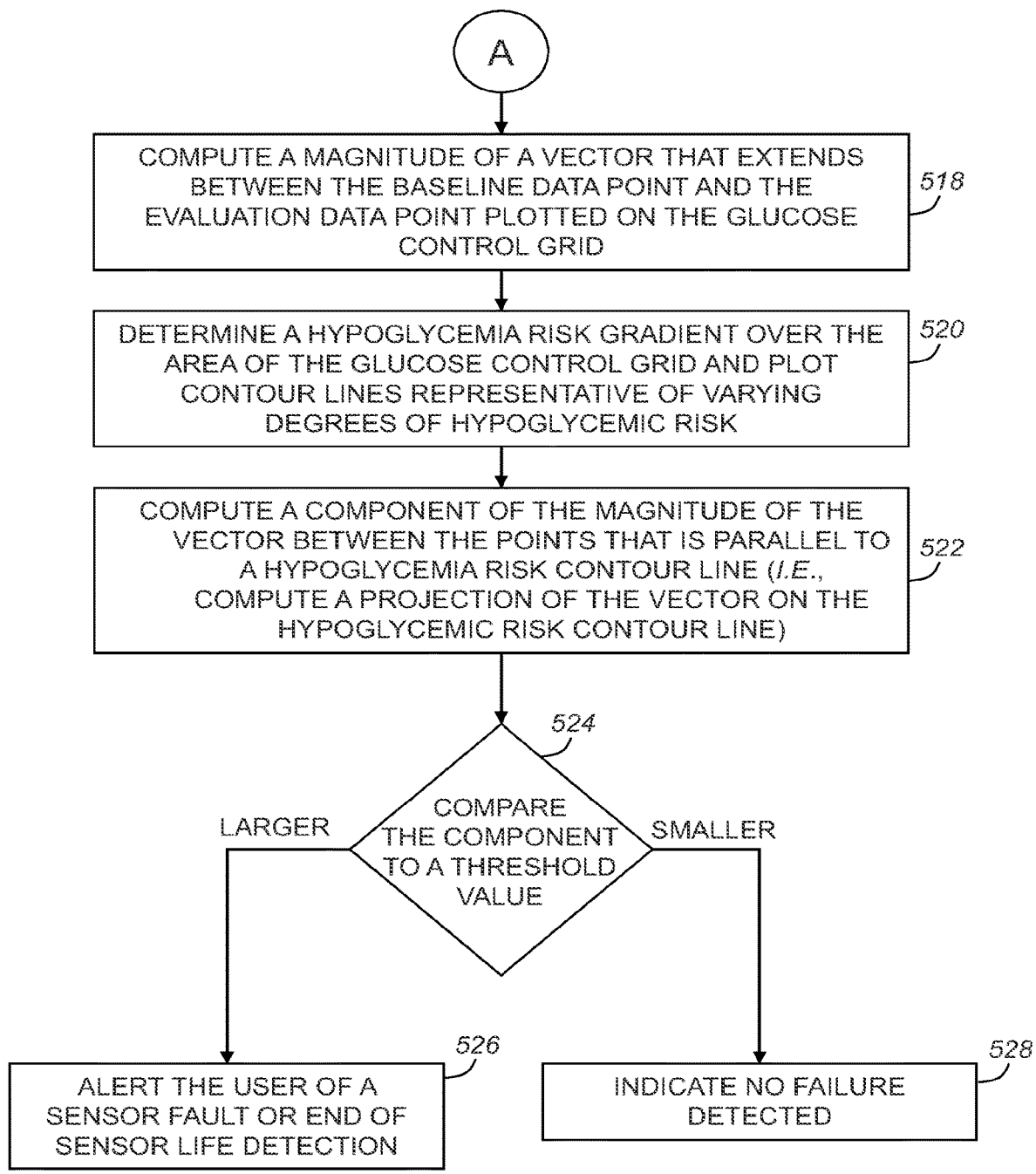

Turning now to FIGS. 5A and 5B, a flowchart depicting an example method 500 of detecting a sensor fault based on analyte sensor data pattern comparison is provided. As noted above, although the following example is described with respect to a glucose sensor, the invention is applicable to any analyte sensor. A first dataset of glucose values is received from sensor electronics coupled to a glucose sensor (502). Based on this first dataset, a baseline median glucose value is computed (504). Alternatively, a mean, a mode, or any other representative "static" value of the first dataset may be used. As used herein, the term median is intended to encompass all such possible values. Also based on this first dataset, a baseline glucose variability value is computed (506). A glucose variability value can be computed in a number of ways. For example, glucose variability may be computed by taking the difference between the median value and the 10th percentile value. Other methods and percentiles, such as standard deviation, inter quartile range, or other second moment calculation, can be used. Using the baseline median glucose value and the baseline glucose variability value as paired coordinate values on a glucose control grid, a baseline data point is plotted on the control grid (508). Alternatively, these values may simply be stored for later use in, for example, a memory.

A second dataset of glucose values is received from the sensor electronics coupled to a glucose sensor (510). To insure the accuracy of the present method, the second dataset should not include a significant number of sensor data that is also part of the first dataset. In other words, the datasets should not overlap in time. For example, the second dataset should have less than five percent of its glucose values in common with the first dataset. Based on this second dataset, an evaluation median glucose value is computed (512). Also based on the second dataset, an evaluation glucose variability value is computed (514). Using the evaluation median glucose value and the evaluation glucose variability value as coordinate values on the glucose control grid, an evaluation data point is plotted on the control grid (516). Alternatively, these values may simply be stored for later use in, for example, the memory.

Next, the magnitude of a vector extending from the baseline data point to the evaluation data point can be computed (518). A hypoglycemia risk gradient over the area of the glucose control grid is determined and risk contour lines representative of varying degrees of hypoglycemic risk are plotted (520). Alternatively, a hypoglycemia risk line that passes through the baseline data point may simply be stored in the memory of the system. A component of the magnitude of the vector extending between the data points that is parallel to one of the hypoglycemia risk contour lines is computed (522). In other words, a projection of the vector on the hypoglycemia risk contour line is computed. For example, the projection may be computed by taking the dot product between the vector extending from the baseline data point to the evaluation data point and a unit vector that describes the slope of the hypoglycemia risk contour lines. If the hypoglycemia risk contour lines are not parallel to each other, then the dot product between the vector and the unit vector that describes the local slope of the hypoglycemia risk line evaluated at the control grid coordinate of the baseline data point can be used.

Once the component of the magnitude that is parallel to a hypoglycemia risk contour line has been computed, it is compared to a threshold value (524). The threshold value may be determined a priori by analyzing a dataset from many patients spanning different levels of glycemic control, different percentages of overlap, and a good representation of nominal sensors and sensors with a fault. Different threshold values are evaluated for their false negatives and false positives. A threshold with appropriately low levels of false positive and false negative rates is chosen. If the component is larger than the threshold value, the system alerts the user that a fault has occurred or that the end of the sensor's life has been detected (526). If the component is smaller than the threshold value, the system indicates that the sensor is functioning properly (528).

Figure 6:
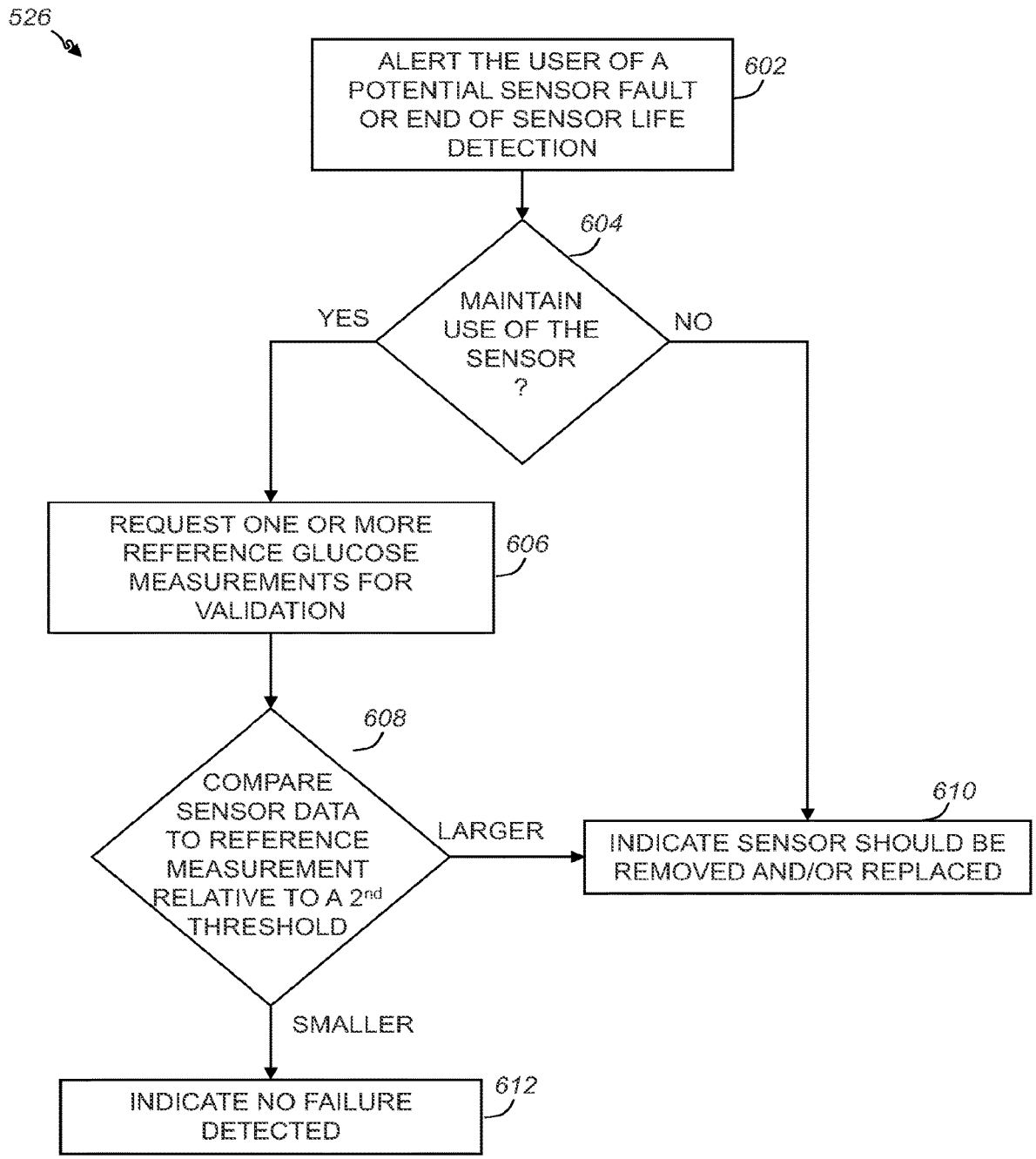
FIG. 6 depicts a flowchart illustrating example details of Box 526 of FIG. 5B in accordance with some embodiments of the present disclosure.

Turning now to FIG. 6, a flowchart depicting the details of alerting the user of a fault (526) is provided. In some embodiments, the system may initially alert the user that there is only a potential fault (602) and ask the user whether he would like to maintain use of the sensor if possible (604). If so, the system can request one or more in-vivo reference glucose measurements for validation (606). The system may then compare the sensor output to reference glucose measurement(s) relative to a second threshold. This second threshold is not related to the first threshold, in that the second threshold relates sensor output to reference glucose measurements. One example is to examine the difference between the latest sensor output value to the latest reference glucose measurement, and flag for a fault if the difference exceeds, for example, 15 mg/dL. Another example is to examine the ratio between the latest sensor output value to the latest reference glucose measurement, and flag for a fault if the ratio is lower than 0.85 or higher than 1.2. In these two examples, the values 15 mg/dL, 0.85, and 1.2 make up the set of second threshold values.

If the user does not wish to maintain use of the sensor or if the component is larger than the larger threshold value, then the system provides the user with an indication that the sensor should be removed and/or replaced (610). If the component is smaller than the larger threshold value, then the system indicates that no failure has been detected (612).

Figure 7A:
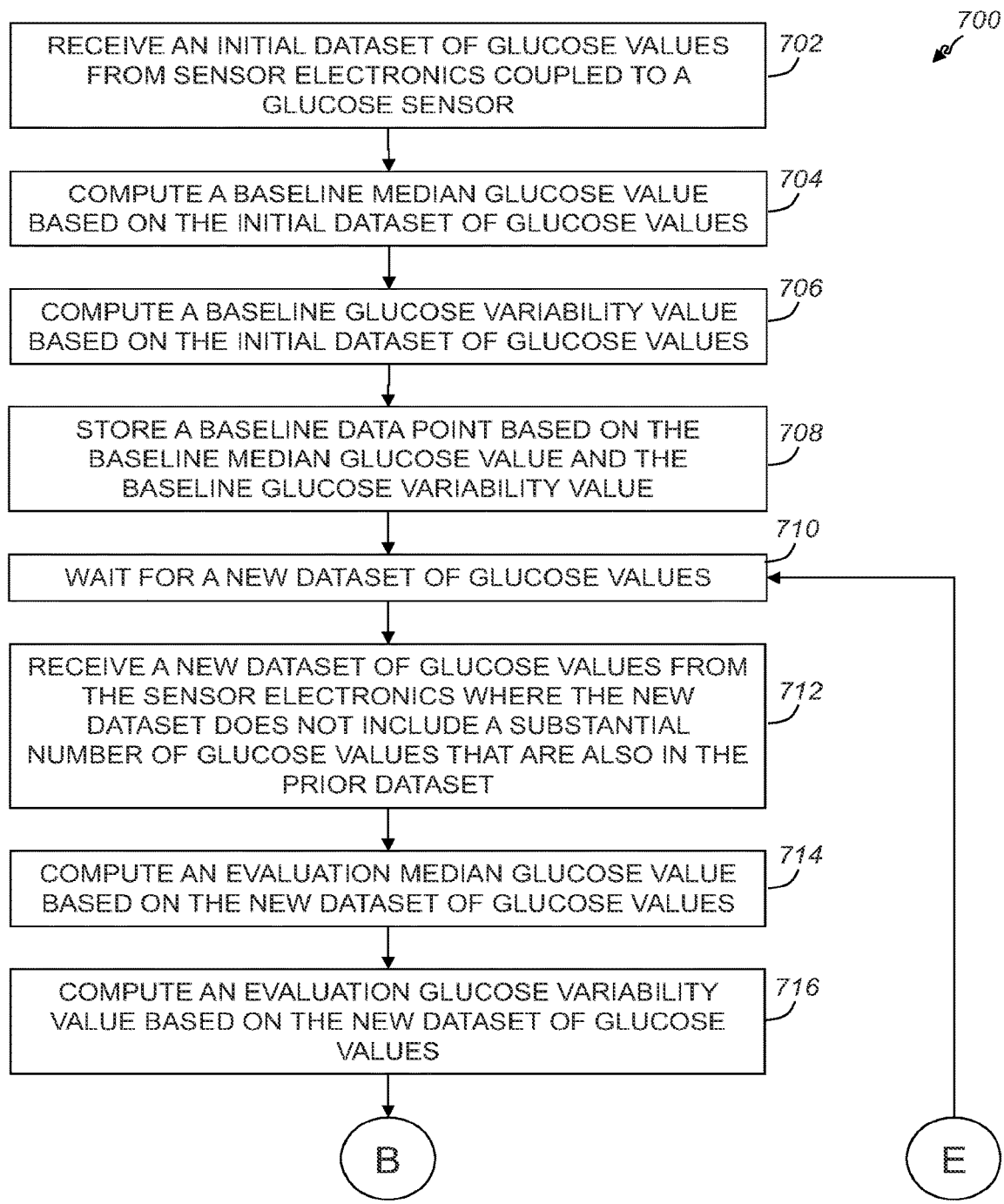
FIGS. 7A to 7C depict a flowchart illustrating an additional example method in accordance with some embodiments of the present disclosure.
Figures 7A, 7B, 7C:
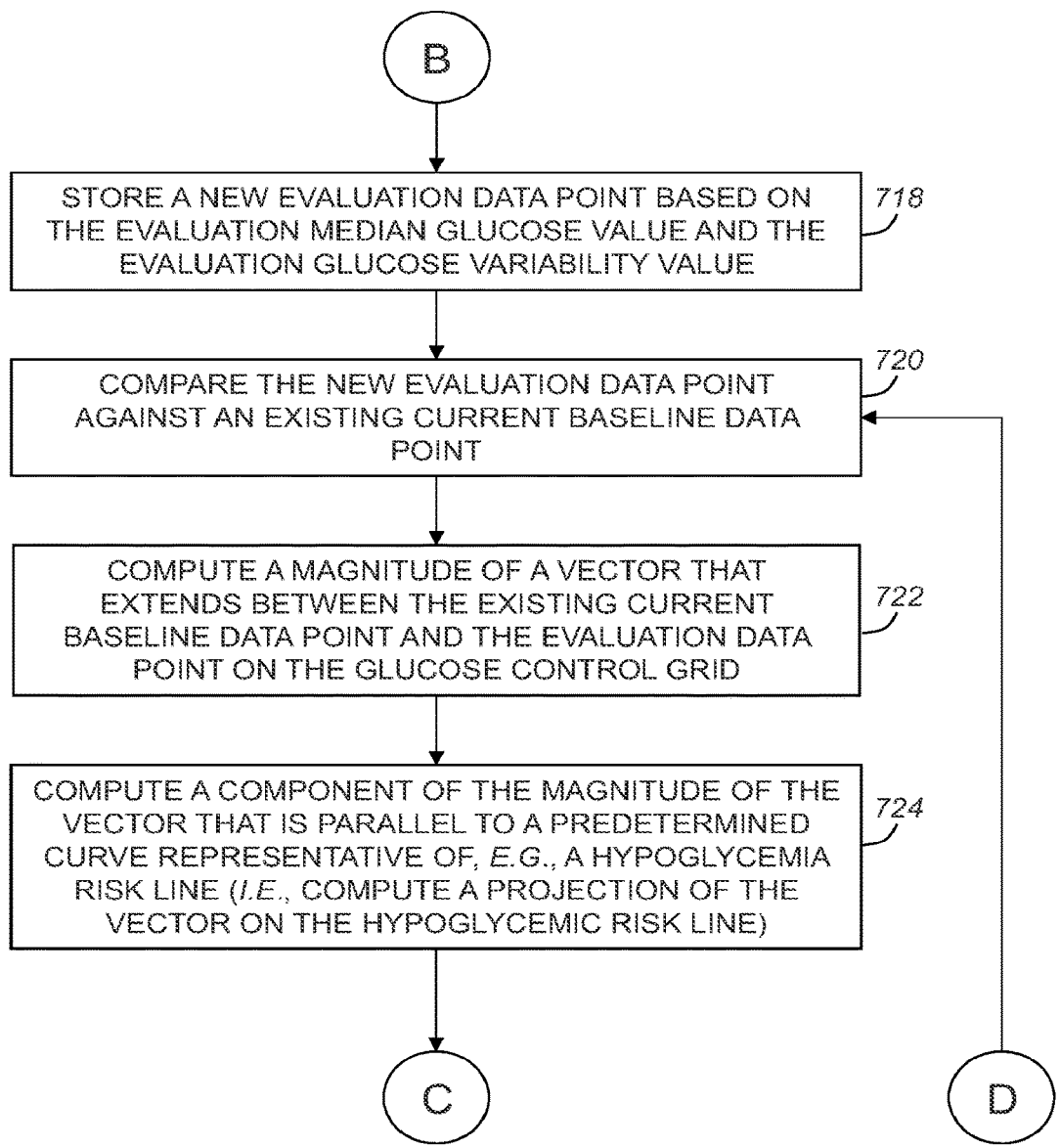
Figure 7C:
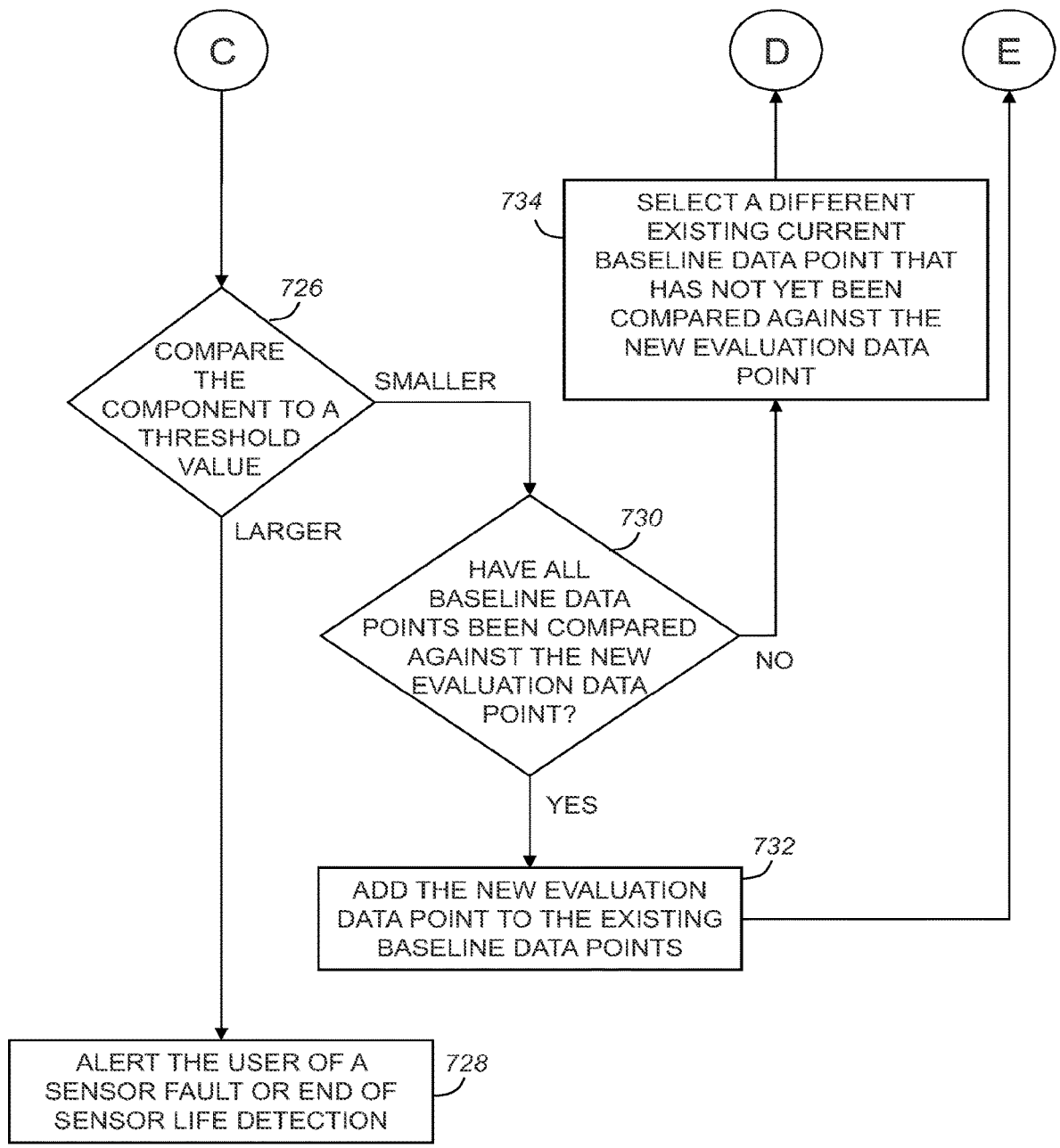

Turning now to FIGS. 7A to 7C, an iterative example embodiment of the method 700 of the present disclosure is provided. An initial dataset of glucose values is received from sensor electronics operatively coupled to a transcutaneously positioned glucose sensor (702). Based on this initial dataset, a baseline median glucose value is computed (704). Also based on the initial dataset of glucose values, a baseline glucose variability value is computed (706). A glucose variability value can be computed in a number of ways. For example, glucose variability may be computed by taking the difference between the median value and the 10th percentile value. Other methods and percentiles can be used. Using the baseline median glucose value and the baseline glucose variability value as coordinate values on a glucose control grid, a baseline data point is stored for later use in, for example, a memory (708). The system then waits for a new dataset of glucose values (710).

A new dataset of glucose values is received from the sensor electronics (712). To insure the accuracy of the present method, the new dataset should not include a significant number of sensor data that is also part of the prior dataset. In other words, the datasets should not overlap in time. For example, the new dataset should have less than five percent of its glucose values in common with the prior dataset. Based on this new dataset, an evaluation median glucose value is computed (714). Also based on the new dataset, an evaluation glucose variability value is computed (716). Using the evaluation median glucose value and the evaluation glucose variability value as coordinate values on the glucose control grid, a new evaluation data point is stored for later use in, for example, the memory (718).

Next, the new evaluation data point is compared against an existing current baseline data point (720). The magnitude of a vector extending from the existing current baseline data point to the new evaluation data point can be computed (722). A component of the magnitude of the vector extending between the data points that is parallel to a predetermined curve representative of, for example, a hypoglycemia risk line is computed (724). In other words, a projection of the vector on a hypoglycemic risk line is computed. For example, the projection may be computed by taking the dot product between the vector extending from the baseline data point to the evaluation data point and a unit vector that describes the slope of the hypoglycemia risk contour lines. If the hypoglycemia risk contour lines are not parallel to each other, then the dot product between the vector and the unit vector that describes the local slope of the hypoglycemia risk line evaluated at the control grid coordinate of the baseline data point can be used.

Once the component of the magnitude that is parallel to a hypoglycemia risk line has been computed, it is compared to a threshold value (726). The threshold value may be determined a priori by analyzing a dataset from many patients spanning different levels of glycemic control, different percentages of overlap, and a good representation of nominal sensors and sensors with a fault. Different threshold values are evaluated for their false negatives and false positives. A threshold with appropriately low levels of false positive and false negative rates is chosen. If the component is larger than the threshold value, the system alerts the user that a fault has occurred or that the end of the sensor's life has been detected (728). If the component is smaller than the threshold value, the system checks for additional baseline data points to compare with the new evaluation data point (730). If all baseline data points have been compared against the new evaluation data point, then the new evaluation data point is added to the existing baseline data points for future comparisons (732) and the system returns to waiting for another new dataset of glucose values (710). If all baseline data points have not been compared against the new evaluation data point, then a different existing baseline data point that has not yet been compared against the new evaluation data point is selected as the current baseline data point (734) and the system returns to comparing the new evaluation data point against the current baseline data point (720). Thus, the system will compare each new evaluation point against all of the baseline data points and if no fault is detected, the new evaluation data point becomes a baseline data point. Thereby, the collection of baseline data points grows with each new evaluation data point that does not indicate a fault.

In an alternate embodiment, the system and methods of the present disclosure can be used to retrospectively detect a fault mode such as ESA. In such embodiments, datasets representing sensor data measured during an "early sensor wear period" (e.g., the first ten to twenty-four hours from the time of sensor insertion) are used to compute evaluation data points that are compared against datasets representing sensor data measured after the early sensor wear period. The projection of the vector extending from the baseline data point to the evaluation data point along a hypoglycemia risk line is compared to a predefined threshold value as with previously described embodiments. However, the predefined threshold value may be different for detecting ESA than for detecting other faults. For example, the threshold value may be determined a priori by analyzing a dataset from many patients spanning different levels of glycemic control, different percentages of overlap, and a good representation of nominal sensors and sensors with ESA. Different threshold values are evaluated for their false negatives and false positives. A threshold with appropriately low levels of false positive and false negative rates is chosen. If the projection is larger than the predefined threshold, the data collected during the early sensor wear period is marked as invalid in the memory of the system. Where the user interface of the system allows for the viewing of any early sensor wear period data, the appropriate segments are indicated as invalid and an alert is issued to the user.

In the manner described above, in accordance with embodiments of the present disclosure, there is provided a computer-implemented method, comprising storing a baseline data point in a memory wherein the baseline data point is representative of a first point on a glucose control grid, storing an evaluation data point in the memory wherein the evaluation data point is representative of a second point on the glucose control grid, computing a magnitude of a vector that would extend between the baseline data point and the evaluation data point if plotted on the glucose control grid, defining a gradient function over an area of the glucose control grid and determining gradient contour lines around the baseline data point and the evaluation data point, computing a component of the magnitude of the vector between the baseline data point and the evaluation data point that is parallel to a contour line of the defined gradient function, comparing the component of the magnitude of the vector to a predefined threshold value, and displaying, on a system display, an indication that a sensor fault has been detected if the component of the magnitude of the vector is greater than a first predefined threshold value.

In certain embodiments, the baseline data point is determined based on using a baseline median glucose value and a baseline glucose variability value as coordinates for the baseline data point, and the baseline median glucose value and the baseline glucose variability value are computed by a processor based on a first dataset of glucose values received from a first data communication from sensor electronics operatively coupled to a transcutaneously positioned glucose sensor.

In certain embodiments, the evaluation data point is determined based on using an evaluation median glucose value and an evaluation glucose variability value as coordinates for the evaluation data point, and the evaluation median glucose value and the evaluation glucose variability value are computed using the processor based on a second dataset of glucose values received from a second data communication from the sensor electronics operatively coupled to the transcutaneously positioned glucose sensor, where the second dataset of glucose values includes glucose values that are not in the first dataset of glucose values.

In certain embodiments, the computer-implemented method further includes displaying, on the system display, the indication that the sensor fault has not been detected if the component of the magnitude of the vector is less than the first predefined threshold value.

In certain embodiments, displaying the indication that the sensor fault has been detected further includes prompting a user to indicate whether to maintain use of a glucose sensor.

In certain embodiments, displaying the indication that the sensor fault has been detected further includes requesting a reference glucose measurement for validation.

In certain embodiments, displaying the indication that the sensor fault has been detected further includes comparing sensor output to the reference glucose measurement relative to a second predefined threshold value.

In certain embodiments, displaying the indication that the sensor fault has been detected further includes displaying, on the system display, an indication to remove the glucose sensor if the component of the magnitude of the vector is greater than a second predefined threshold value.

A system for determining analyte concentration in blood based on analyte concentration measured in interstitial fluid in certain embodiments includes a processor, and a memory coupled to the processor, the memory storing processor executable instructions to: store a baseline data point in the memory wherein the baseline data point is representative of a first point on an analyte control grid, store an evaluation data point in the memory wherein the evaluation data point is representative of a second point on the analyte control grid, compute a magnitude of a vector that would extend between the baseline data point and the evaluation data point if plotted on the analyte control grid, define a gradient function over an area of the analyte control grid and determine gradient contour lines around the baseline data point and the evaluation data point, compute a component of the magnitude of the vector between the baseline data point and the evaluation data point that is parallel to a contour line of the defined gradient function, compare the component of the magnitude of the vector to a predefined threshold value, display, on a system display, an indication that a sensor fault has been detected if the component of the magnitude of the vector is greater than a first predefined threshold value.

In certain embodiments, the memory is further configured to store processor executable instructions to: receive a first dataset of analyte values from sensor electronics operatively coupled to a transcutaneously positioned analyte sensor, compute a baseline median analyte value based on the first dataset of analyte values, compute a baseline analyte variability value based on the first dataset of analyte values, determine the baseline data point based on using the baseline median analyte value and the baseline analyte variability value as coordinates for the baseline data point on the analyte control grid.

In certain embodiments, the memory is further configured to store processor executable instructions to: receive a second dataset of analyte values from the sensor electronics where the second dataset of analyte values includes analyte values that are not in the first dataset of analyte values, compute an evaluation median analyte value based on the second dataset of analyte values, compute an evaluation analyte variability value based on the second dataset of analyte values, determine the evaluation data point based on using the evaluation median analyte value and the evaluation analyte variability value as coordinates for the evaluation data point on the analyte control grid.

In certain embodiments, the memory is further configured to store processor executable instructions to display, on the system display, the indication that the sensor fault has not been detected if the component of the magnitude of the vector is less than the first predefined threshold value.

In certain embodiments, the memory is further configured to store processor executable instructions to display, on the system display, the indication that the sensor fault has been detected further includes an instruction to prompt a user to indicate whether to maintain use of a sensor.

In certain embodiments, the instruction to display, on the system display, the indication that the sensor fault has been detected further includes an instruction to request a reference glucose measurement for validation.

In certain embodiments, the instruction to display, on the system display, the indication that the sensor fault has been detected further includes an instruction to compare sensor output to the reference glucose measurement relative to a second predefined threshold value.

In certain embodiments, the instruction to display, on the system display, the indication that the sensor fault has been detected further includes an instruction to display, on the system display, an indication to remove the sensor if the component of the magnitude of the vector is greater than the second predefined threshold value.

A computer-implemented method in certain embodiments includes storing an evaluation data point representative of a first point on a glucose control grid, storing a baseline data point representative of a second point on the glucose control grid, computing a magnitude of a vector that extends between the baseline data point and the evaluation data point, defining a gradient function over an area of the glucose control grid including determining at least one gradient contour line around the baseline data point and the evaluation data point, computing a component of the magnitude of the vector between the baseline data point and the evaluation data point that is parallel to a contour line of the defined gradient function, comparing the component of the magnitude of the vector to a predefined threshold value, displaying, on a system display, an indication that an early signal attenuation (ESA) fault has been detected if the component of the magnitude of the vector is greater than a first predefined threshold value.

In certain embodiments, the method further includes receiving during an early wear period, a first dataset of glucose values from sensor electronics operatively coupled to a transcutaneously positioned glucose sensor, computing an evaluation median glucose value based on the first dataset of glucose values, computing an evaluation glucose variability value based on the first dataset of glucose values, determining the evaluation data point based on using the evaluation median glucose value and the evaluation glucose variability value as coordinates for the evaluation data point on the glucose control grid.

In certain embodiments, the method further comprises receiving after the early wear period a second dataset of glucose values from the sensor electronics where the second dataset of glucose values does not include glucose values that are also in the first dataset of glucose values, computing a baseline median glucose value based on the second dataset of glucose values, computing a baseline glucose variability value based on the second dataset of glucose values, and determining the baseline data point based on using the baseline median glucose value and the baseline glucose variability value as coordinates for the baseline data point on the glucose control grid.

In certain embodiments, the method further comprises displaying the indication that the early signal attenuation (ESA) fault has not been detected if the component of the magnitude of the vector is less than the first predefined threshold value.

In certain embodiments, the method further comprises displaying the indication that the early signal attenuation (ESA) fault has been detected further includes prompting a user whether to maintain use of a glucose sensor.

In certain embodiments, the method further comprises displaying the indication that the early signal attenuation (ESA) fault has been detected further includes requesting a reference glucose measurement for validation.

In certain embodiments, displaying the indication that the early signal attenuation (ESA) fault has been detected further includes comparing sensor output to the reference glucose measurement relative to a second predefined threshold value.

In certain embodiments, displaying the indication that the early signal attenuation (ESA) fault has been detected further includes displaying, on the system display, an indication that a first dataset of glucose values are invalid.

In certain embodiments, the method further comprises storing the evaluation data point as the baseline data point if no fault is detected for the evaluation data point.

In certain embodiments, the method further comprises comparing the evaluation data point against multiple baseline data points.

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:
1. A computer-implemented method, comprising:
computing a magnitude of a vector extending from a baseline analyte data point to an evaluation analyte data point;
computing a component of the magnitude of the vector between the baseline analyte data point and the evaluation analyte data point that is parallel to a hypoglycemic risk contour line;
determining whether the component of the magnitude of the vector is greater than a first threshold value; and
displaying, based on the determination, an analyte sensor fault indication on a display.
2. The computer-implemented method of claim 1, further comprising:

determining a baseline median glucose value and a baseline glucose variability value; and determining the baseline analyte data point based on the baseline median glucose value and the baseline glucose variability value.

3. The computer-implemented method of claim 2, wherein determining the baseline median glucose value and the baseline glucose variability value comprises determining the baseline median glucose value and the baseline glucose variability value based on a first dataset of glucose values.

4. The computer-implemented method of claim 2, further comprising:

determining an evaluation median glucose value and an evaluation glucose variability value; and determining the evaluation analyte data point based on the evaluation median glucose value and the evaluation glucose variability value.

5. The computer-implemented method of claim 4, wherein determining the baseline median glucose value and the baseline glucose variability value comprises determining the baseline median glucose value and the baseline glucose variability value based on a first dataset of glucose values, wherein determining the evaluation median glucose value and the evaluation glucose variability value comprises determining the evaluation median glucose value and the evaluation glucose variability value based on a second dataset of glucose values, and wherein the second dataset of glucose values includes glucose values that are not in the first dataset of glucose values.

6. The computer-implemented method of claim 1, wherein the analyte sensor fault indication is indicative that an analyte sensor fault has been detected.

7. The computer-implemented method of claim 6, wherein determining whether the component of the magnitude of the vector is greater than the first threshold value comprises determining that the component of the magnitude of the vector is greater than the first threshold value.

8. The computer-implemented method of claim 6, wherein the analyte sensor fault indication includes information regarding whether to maintain use of a glucose sensor.

9. The computer-implemented method of claim 6, wherein the analyte sensor fault indication includes a request for a reference glucose measurement.

10. The computer-implemented method of claim 1, wherein the analyte sensor fault indication is indicative that an early signal attenuation (ESA) fault has been detected.

11. The computer-implemented method of claim 10, wherein determining whether the component of the magnitude of the vector is greater than the first threshold value comprises determining that the component of the magnitude of the vector is greater than the first threshold value.

12. The computer-implemented method of claim 10, wherein the analyte sensor fault indication includes information regarding whether to maintain use of a glucose sensor.

13. The computer-implemented method of claim 10, wherein the analyte sensor fault indication includes a request for a reference glucose measurement.

14. The computer-implemented method of claim 1, wherein the analyte sensor fault indication is indicative that an analyte sensor fault has not been detected.

15. The computer-implemented method of claim 14, wherein determining whether the component of the magnitude of the vector is greater than the first threshold value comprises determining that the component of the magnitude of the vector is less than the first threshold value.

16. The computer-implemented method of claim 1, wherein the analyte sensor fault indication is indicative that an early signal attenuation (ESA) fault has not been detected.

17. The computer-implemented method of claim 16, wherein determining whether the component of the magnitude of the vector is greater than the first threshold value comprises determining that the component of the magnitude of the vector is less than the first threshold value.

18. A non-transitory computer-readable medium having software stored thereon that, when executed by a processor, causes the processor to:

compute a magnitude of a vector extending from a baseline analyte data point to an evaluation analyte data point;

compute a component of the magnitude of the vector between the baseline analyte data point and the evaluation analyte data point that is parallel to a hypoglycemic risk contour line;

determine whether the component of the magnitude of the vector is greater than a first threshold value; and cause, based on the determination, an analyte sensor fault indication to be displayed on a display.

19. A processor configured to:

compute a magnitude of a vector extending from a baseline analyte data point to an evaluation analyte data point;

compute a component of the magnitude of the vector between the baseline analyte data point and the evaluation analyte data point that is parallel to a hypoglycemic risk contour line;

determine whether the component of the magnitude of the vector is greater than a first threshold value; and cause, based on the determination, an analyte sensor fault indication to be displayed on a display.

* * * * *